(12) United States Patent
Witte et al.

(10) Patent No.: US 8,882,855 B2
(45) Date of Patent: Nov. 11, 2014

(54) GEL-BASED OXIDATION COLORANT INCLUDING AN EMULSIFIER COMBINATION AND THICKENER

(71) Applicant: Henkel AG & Co. KGaA, Düsseldorf (DE)

(72) Inventors: Christiane Witte, Hetlingen (DE); Hartmut Manneck, Barnitz (DE)

(73) Assignee: Henkel AG & Co. KGAA, Duesseldorf (DE)

( * ) Notice: Subject to any disclaimer, the term of this patent is extended or adjusted under 35 U.S.C. 154(b) by 0 days.

(21) Appl. No.: 14/288,536

(22) Filed: May 28, 2014

(65) Prior Publication Data

US 2014/0259453 A1 Sep. 18, 2014

Related U.S. Application Data

(63) Continuation of application No. PCT/EP2012/071796, filed on Nov. 5, 2012.

(30) Foreign Application Priority Data

Dec. 16, 2011 (DE) .......................... 10 2011 088 819

(51) Int. Cl.
| | |
|---|---|
| *A61Q 5/10* | (2006.01) |
| *A61K 8/34* | (2006.01) |
| *A61K 8/04* | (2006.01) |
| *A61K 8/81* | (2006.01) |
| *A61K 8/92* | (2006.01) |
| *A61K 8/86* | (2006.01) |
| *A61K 8/39* | (2006.01) |

(52) U.S. Cl.
CPC ................. *A61K 8/042* (2013.01); *A61K 8/345* (2013.01); *A61K 8/8152* (2013.01); *A61K 8/922* (2013.01); *A61Q 5/10* (2013.01); *A61K 8/86* (2013.01); *A61K 8/39* (2013.01)
USPC ................. 8/405; 8/406; 8/552; 8/558; 8/580

(58) Field of Classification Search
USPC .............................. 8/405, 406, 552, 558, 580
See application file for complete search history.

(56) References Cited

U.S. PATENT DOCUMENTS

2007/0192968 A1* 8/2007 Schmenger et al. ............... 8/405

FOREIGN PATENT DOCUMENTS

| DE | 102006005768 | | 8/2007 |
|---|---|---|---|
| EP | 1634572 | A1 | 3/2006 |
| EP | 2340807 | A2 | 7/2011 |
| WO | 8800823 | | 2/1988 |
| WO | 9701323 | A1 | 1/1997 |
| WO | 20050067874 | | 7/2005 |
| WO | 2006015650 | A1 | 2/2006 |

OTHER PUBLICATIONS

KH. Schrader: 'Grundlagen und Rezepturen der Kosmetika', (translation Basics and recipes of cosmetics), 2., verbesserte und erweiterte Auflage, 1989, Huthig Buch Verlag Heidelberg, pjs 1-20 (book table of contents), English abstract machine translation only.

* cited by examiner

*Primary Examiner* — Eisa Elhilo
(74) *Attorney, Agent, or Firm* — Steven L. Nichols; Van Cott, Bagley, Cornwall & McCarthy P.C.

(57) ABSTRACT

The present specification provides for an agent for dyeing keratinic fibers. The agent includes, in a gel-like carrier at least one oxidation dye precursor. The gel-like carrier includes at least one emulsifier combination. The emulsifier combination includes one or more non-ionic polyethoxylated emulsifiers selected from ethoxylated fatty alcohols containing between 8 and 22 carbon atoms, ethoxylated castor oil, or combinations thereof, and one or more polyethylene glycols having an average molecular weight between 100 and 100,000 grams per mole (g-MOL$^{-1}$). The gel-like carrier also includes at least one polymeric thickener selected from homopolymers of acrylic acid or methacrylic acid, copolymers of acrylic acid or methacrylic acid with $C_1$-$C_4$ alkyl esters of acrylic acid or methacrylic acid, or combinations thereof.

20 Claims, No Drawings

continued from previous page …

GEL-BASED OXIDATION COLORANT INCLUDING AN EMULSIFIER COMBINATION AND THICKENER

RELATED DOCUMENTS

The present specification is a U.S. continuation patent application under 35 U.S.C. 111(a) and claims the right of priority under 35 U.S.C. 365 to international patent Application No. PCT/EP2012/071796, filed Nov. 5, 2012, entitled "Gel-Based Oxidation Colorant Comprising an Emulsifier Combination and Thickener" which claims benefit of German application No. 10 2011 088 819.5, filed Dec. 16, 2011, these applications are herein incorporated by reference in their entirety.

FIELD OF THE INVENTION

The present application relates generally to an agent for oxidatively dyeing keratinic fibers. More specifically, the present application relates to an agent characterized by a gel-like basis of a specific combination of emulsifiers and a polymeric thickener.

BACKGROUND OF THE INVENTION

Modifying the shape and color of hair is an important area of modern cosmetics. A consumer uses color-changing agents for fashionable hair style color schemes or for concealing gray, or even white, hair with fashionable or natural color tints. In addition to the desired coloration power, these agents should cause the least possible damage to the hair and preferably may even possess additional care characteristics.

There are a number of diverse dying systems for the provision of color-changing cosmetic agents, especially for hair. An oxidation dye is used for long-lasting, intensive colorations with corresponding fastness characteristics. Such dyes usually include oxidation dye precursors, "developer components," and "coupler components." Under the influence of oxidizing agents, or from atmospheric oxygen, the developer components form the actual colorants among each other or by coupling with one or more coupler components. In spite of their advantageous coloration properties, oxidative hair dyeing agents are afflicted with disadvantages for the user.

First, the use of these oxidizing agents for developing the actual coloration and the basic pH needed for dyeing damages the hair structure and the hair surface. However, there is still a need for agents with improved dyeing power. In particular, agents resulting in improved, uniform colorations with high intensity and vividness as well as a good gray coverage capability (in particular on differently treated hair) are a continued focus of development. As both the resultant coloration and the associated stress on the hair fibers depend on the contact time of the agent, there may exist a need to monitor the coloration progress during the dyeing procedure, such that the desired end point of the treatment can be exactly determined. Doing so may minimize stresses on the hair fibers in addition to improving the desired coloration result. It is also desirable to provide a transparent or clear dye preparation.

Finally, current hair dyes, due to the plurality of ingredients, have been shown to frequently possess unsatisfactory rheological properties. These are particularly evident from the viscosity fluctuations during storage and application. For example, agents that thicken during storage are associated with problems such as withdrawal, dosing, and application. Whereas agents that decrease in viscosity during storage have inadequate application characteristics.

Consequently, an object of the present specification is to mitigate the abovementioned disadvantages of oxidative hair dyes. By detecting the end point of the treatment, the dyes may cause less damage to the hair. In particular, protection against oxidative damage to the hair structure and hair surface are achieved by means of the hair dye. At the same time, the dye may possess improved rheological properties that, in particular, offer improved viscosity stability and shear sensitivity. In addition, the dye may enable improved color intensity and improved gray coverage compared with conventional dyes.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

The present specification describes an agent for dyeing keratinic fibers. The agent includes, in a gel-like carrier, at least one oxidation dye precursor. The gel-like carrier includes at least one emulsifier combination. The at least one emulsifier combination includes one or more non-ionic polyethoxylated emulsifiers selected from 1) ethoxylated fatty alcohols containing between 8 and 22 carbon atoms, 2) ethoxylated castor oil, or 3) combinations thereof. The emulsifier combination also includes one or more polyethylene glycols having an average molecular weight between 100 and 100,000 grams per mole (g-MOL$^{-1}$). The gel-like carrier also includes at least one polymeric thickener selected from 1) homopolymers of acrylic acid or methacrylic acid, 2) copolymers of acrylic acid or methacrylic acid with $C_1$-$C_4$ alkyl esters of acrylic acid or methacrylic acid, or 3) combinations thereof.

The present specification describes a kit for dyeing keratinic fibers. The kit includes at least two containers assembled separately from one another. A first container holds an agent. The agent includes, in a gel-like carrier, at least one oxidation dye precursor. The gel-like carrier includes at least one emulsifier combination. The emulsifier combination includes one or more non-ionic polyethoxylated emulsifiers selected from ethoxylated fatty alcohols containing between 8 and 22 carbon atoms, ethoxylated castor oil, or combinations thereof and one or more polyethylene glycols having an average molecular weight between 100 and 100,000 grams per mole (g-MOL$^{-1}$). The gel-like carrier also includes at least one polymeric thickener, selected from homopolymers of acrylic acid or methacrylic acid, copolymers of acrylic acid or methacrylic acid with $C_1$-$C_4$ alkyl esters of acrylic acid or methacrylic acid, or combinations thereof. A second container holds an oxidizing agent preparation that includes at least hydrogen peroxide in a physiologically acceptable carrier.

The present specification describes a method for dyeing human hair. The method includes blending an agent with an oxidizing agent preparation before application to form a ready-to-use agent. The agent includes, in a gel-like carrier, at least one oxidation dye precursor. The gel-like carrier includes 1) at least one emulsifier combination. The emulsifier combination includes a) one or more non-ionic polyethoxylated emulsifiers, selected from ethoxylated fatty alcohols containing between 8 and 22 carbon atoms, ethoxylated castor oil, or combinations thereof and b) one or more polyethylene glycols having an average molecular weight between 100 and 100,000 grams per mole (g-MOL$^{-1}$). The gel-like carrier also includes 2) at least one polymeric thickener selected from homopolymers of acrylic acid or methacrylic acid, copolymers of acrylic acid or methacrylic acid with $C_1$-$C_4$ alkyl esters of acrylic acid or methacrylic acid, or combinations thereof. The oxidizing agent preparation includes at least hydrogen peroxide in a physiologically acceptable carrier. The method includes applying the ready-to-use agent onto the hair, leaving the ready-to-use agent on the hair for a period of 5 to 45 minutes, and rinsing the hair.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present specification describes a novel dye preparation matrix based on a gel-like carrier that includes an emulsifier combination of certain non-ionic, polyethoxylated emulsifiers and certain polyethylene glycol(s), the pylyethylene glycol(s) having an average molecular weight of 100 to 100,000 grams per mole (g $mol^{-1}$). The gel-like carrier also includes a polymeric thickener that enables the provision of transparent dyes with high viscosity stability and at the same time enables the progress of the coloration to be observed.

Accordingly, the first subject matter of the present specification is an agent for dyeing keratinic fibers, in particular human hair, which includes at least one oxidation dye precursor in a gel-like carrier. The gel-like carrier of the dye includes:

a) at least one emulsifier combination that includes:
  i) one or more non-ionic, polyethoxylated emulsifiers selected from ethoxylated fatty alcohols containing 8 to 22 carbon atoms, ethoxylated castor oil, or combinations thereof, and
  ii) one or more polyethylene glycol(s) having an average molecular weight of 100 to 100,000 g $mol^{-1}$, and
b) and at least one polymeric thickener selected from homopolymers of acrylic acid or methacrylic acid, copolymers of acrylic acid or methacrylic acid with $C_1$-$C_4$ alkyl esters of acrylic acid or methacrylic acid, or combinations thereof.

The agents of the present specification are characterized by good coloration properties with concomitant protection against damage to human hair. In particular, the agents of the present specification enable uniform dyeing with a high color intensity and good fastness. Finally, the agents of the present specification possess significant advantages in regard to the viscosity stability during storage and application. Furthermore, the dye preparations are characterized by an optical transparency that enables the progress of the color development to be visually monitored.

As used in the present specification and in the appended claims, the term "keratinic fibers," "keratin fibers," and similar terminology are understood to mean furs, wool, feathers, and particularly human hair. Although the agents according to the present specification are primarily suitable for dyeing keratin fibers, in principle nothing prevents their use in other fields.

The agents according to the present specification include the dye precursors in a gel-like carrier. This gel-like carrier is preferably optically transparent. The gel-like carrier particularly preferably retains its optical transparency even after mixing with an oxidizing agent preparation to form a ready-to-use oxidation dye. As used in the present specification and in the appended claims, the term "optical transparency" is understood to mean the visual recognizability of the color development on the hair fiber after the dye has been applied. The resulting coating thickness of the dye preparation on the hair fiber may be in the range 0.00001 millimeters (mm) to 0.1 mm.

Consequently, optically transparent gels may also be described by the term "clear gel-like carrier." Here, the agents do not exist as an emulsion or lipo/oleogel. Therefore, the agents preferably do not include fatty substances. In one example of the first subject matter of the present specification, the agents are free of fatty materials, in particular free of fatty alcohols, hydrophobic fatty acid esters and mineral fatty materials. As used in the present specification and in the appended claims, the term "free of fatty materials" is understood to mean a content of at most 0.5 weight percent (wt %), preferably at most 0.1 wt % and further preferably at most 0.01 wt %, each relative to the total weight of the agent. In the context of the present specification, fatty materials are characterized by a water-solubility of less than 0.1 grams per liter (g/L) under standard conditions. In this regard, fatty alcohols are linear, saturated or unsaturated alkane-1-ols containing 8 to 24 carbon atoms such as cetyl alcohol, stearyl alcohol or oleyl alcohol. Hydrophobic acid esters in this regard are fatty acid triglycerides without additional hydrophilic structural elements such as in olive oil or cocoa fat, fatty acid diesters with diols such as ethylene glycol distearate, and fatty acid esters with alkanols such as isopropyl myristate or jojoba oil. In this regard, mineral fatty substances are hydrocarbons such as polyethylene, Vaseline or paraffin.

In the context of the present specification, the gel-like carrier is aqueous, alcoholic or aqueous-alcoholic. As used in the present specification and in the appended claims, the term "aqueous-alcoholic carriers" refer to water-containing solutions, including 3 to 70% by weight of a $C_1$-$C_4$ alcohol, in particular, ethanol or isopropanol, based on the total weight of the application mixture. The agents according to the present specification may additionally include further organic solvents, such as for example methoxybutanol, ethyl diglycol, 1,2-propylene glycol, n-propanol, n-butanol, n-butylene glycol, glycerin, diethylene glycol monoethyl ether and diethylene glycol mono-n-butyl ether. Preference here is given to all water-soluble organic solvents. In the context of the present specification, an aqueous carrier includes at least 30 wt %, especially at least 50 wt % water, relative to the total weight of the agent. Aqueous carriers are preferred, such that the agent has a content of at least 80 wt %, preferably at least 85 wt %, relative to the total weight of the agent.

As used in the present specification and in the appended claims, the term "gel-like" means a shape-stable, easily deformable, liquid-rich disperse system that includes at least two components, which consist of 1) a solid, colloidally dispersed substance with long or highly branched particles as the thickener and 2) a liquid (mostly water) as the dispersant. In this regard, the solid substance is coherent, i.e. it forms a spatial network in the dispersant.

As the first essential ingredient, the agent contains in the gel-like carrier at least one emulsifier combination composed of:

i) one or more non-ionic polyethoxylated emulsifier, selected from ethoxylated fatty alcohols containing 8 to 22 carbon atoms, ethoxylated castor oil, or combinations thereof, and
ii) one or more polyethylene glycol(s) having an average molecular weight of 100 to 100,000 g $mol^{-1}$.

In one example, the non-ionic emulsifiers are selected from ethoxylated, linear fatty alcohols, preferably with a chain length of 8 to 22 carbon atoms. As used in the present specification and in the appended claims, the term "ethoxylated fatty alcohol" refers to an addition product of ethylene oxide onto a fatty alcohol, wherein the degree of ethoxylation represents the molar quantity of ethylene oxide (EO) that was added on average per mole fatty alcohol. Preferred ethoxylated fatty alcohols are ethylene oxide addition products onto capric alcohol, lauryl alcohol, isotridecyl alcohol, myristyl alcohol, cetyl alcohol, palmoleyl alcohol, stearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol as well as their industrial mixtures, which result from the high pressure hydrogenation of industrial methyl esters based on fats and oils or aldehydes from Roelen's Oxo synthesis as well as the monomer fraction in the dimerization of unsaturated fatty alcohols. Addition products onto industrial fatty alcohols or their mixtures containing 12 to 18 carbon atoms such as for example coco, palm, palm nut or tallow fatty alcohol are particularly preferred, in particular coco and/or tallow fatty alcohol.

Depending on the method of production, the ethoxylated fatty alcohols of the present specification are obtained as a mixture with a variable distribution of degrees of ethoxylation. In the context of the present specification, these emulsifiers are therefore characterized by their average degree of ethoxylation. This can usually be observed as the number after the fatty alcohol suffix "eth-" in the INCI name. Particularly suitable ethoxylated fatty alcohols are fatty alcohols with a degree of ethoxylation of 12 to 100, preferably 20 to 80 moles ethylene oxide per mole fatty alcohol. Examples are Ceteaeth-12, Ceteth-15, Ceteareth-15, Laneth-16, Ceteth-16, Oleth-16, Steareth-16, Oleth-20, Ceteth-20, Ceteareth-20, Ceteareth-23, Laureth-23, Ceteareth-25, Ceteareth-30, Ceteth-40, Laneth-40, Oeth-50, Ceteareth-50, Ceteareth-60, Ceteareth-80.

In another example, the non-ionic emulsifiers are selected from ethoxylated castor oil. This includes ethoxylated, hardened (i.e. hydrogenated) and unhardened castor oil. The degree of ethoxylation indicates the molar quantity of ethylene oxide (EO) that was added on average per mole castor oil. Preferred ethoxylated castor oils are those known under the INCI names PEG-5 castor oil, PEG-7 hydrogenated castor oil, PEG-10 hydrogenated castor oil, PEG-25 hydrogenated castor oil, PEG-35 castor oil, PEG-36 castor oil, PEG-40 castor oil, PEG-40 hydrogenated castor oil, PEG-50 hydrogenated castor oil, PEG-60 castor oil, PEG-60 hydrogenated castor oil, PEG-80 castor oil, PEG-80 hydrogenated castor oil, PEG-100 castor oil, PEG-100 hydrogenated castor oil, PEG-120 castor oil, PEG-120 hydrogenated castor oil, PEG-150 castor oil, PEG-150 hydrogenated castor oil, PEG-200 castor oil, and PEG-200 hydrogenated castor oil.

Castor oils with an average degree of ethoxylation of 20 to 150, preferably 30 to 100 and particularly preferably 35 to 80 are preferred non-ionic emulsifiers. PEG-40 hydrogenated castor oil is particularly preferred.

In one example, the non-ionic polyethoxylated emulsifiers form 0.1 to 10.0 wt %, preferably 0.3 to 8.0 wt %, particularly preferably 0.5 to 5.0 wt % and in particular 0.8 to 3.0 wt % of the total weight of the agent.

As another essential component, the emulsifier combination includes at least one or more polyethylene glycol(s) having an average molecular weight of 100 to 100,000 g mol$^{-1}$.

In one example, polyethylene glycol(s) are preferred in this regard which have an average molecular weight of 500 to 15,000 g mol$^{-1}$, preferably 1000 to 10,000 g mol$^{-1}$ and particularly preferably 1,200 to 5,000 g mol$^{-1}$. Exemplary suitable polyethylene glycols are PEG-30, PEG-32, PEG-35, PEG-38, PEG-40, PEG-45, PEG-50, PEG-60, PEG-75, PEG-80, PEG-100 (i.e. degree of ethoxylation 30, 32, 35, 38, 40, 50 etc.) or PEG 1000, PEG 1200, PEG 1500, PEG 2000, PEG 3000, PEG 5000, PEG 6000 (i.e. average molecular weight 1000, 1200, 1500, 2000 etc.).

Agents according to the present specification include the polyethylene glycol(s) preferably in 0.1 to 10.0 wt %, preferably 0.3 to 8.0 wt %, particularly preferably 0.5 to 5.0 wt % and in particular 0.8 to 3.0 wt %, relative to the total weight of the agent.

Furthermore, for particularly good transparency, the agents according to the present specification include gel-like carriers with an emulsifier combination of non-ionic, polyethoxylated emulsifiers and polyethylene glycols in a specific weight ratio to one another.

One example of the first subject matter of the present specification is therefore characterized in that the weight ratio of the fraction of the non-ionic, polyethoxylated emulsifiers to the fraction of the polyethylene glycol in the emulsifier combination is 3:1 to 1:3, preferably 2:1 to 1:2 and in particular 1.5:1 to 1:1.5.

The total amount of the emulsifier combination in the agent according to the present specification firstly controls the flow behavior of the agent and the gel stability, and secondly has a positive influence on the solubility of the other ingredients in the agent, thereby reducing haze caused by dispersed ingredients. In some examples, the emulsifier combination in an amount from 0.5 to 15.0 wt % are preferred, preferably 1.0 to 10.0 wt %, particularly preferably 1.5 to 7.5 wt % and in particular 3.0 to 5.0 wt %, relative to the total weight of the agent.

Another example of the first subject matter of the present specification is therefore characterized in that the agent includes the emulsifier combination in an amount of 0.5 to 15.0 wt %, preferably 1.0 to 10.0 wt %, particularly preferably 1.5 to 7.5 wt % and especially 3.0 to 5.0 wt %, relative to the total weight of the agent.

The agents according to the present specification include as a further essential ingredient at least one polymeric thickener, selected from homopolymers of acrylic acid or methacrylic acid, copolymers of acrylic acid or methacrylic acid with $C_1$-$C_4$ alkyl esters of acrylic acid or methacrylic acid, or combinations thereof.

Suitable homopolymers of acrylic acid are optionally crosslinked polyacrylic acids (such as a carbomer which is available under the trade name CARBOPOL® manufactured by Lubrizol for example) as well as polyacrylates as their partially or completely deprotonated salt forms. Here, the acidic groups may be fully or partially present as sodium, potassium, ammonium, mono- or triethanolammonium salts. Allyl ethers of pentaerythritol, of sucrose and of propylene glycol as well as ethylene glycol dimethacrylate are exemplary suitable preferred crosslinking agents. Examples of homopolymers of methacrylic acid are correspondingly the optionally crosslinked polymethacrylic acids and polymethacrylates.

In another example, the agent according to the present specification may include at least one homopolymer or copolymer of anionic acrylic acid and/or methacrylic acid as the polymeric thickener. Preferred polymers of this type are:
  polymers with at least 10 wt % of $C_1$-$C_4$ alkyl esters of acrylic acid, 25 to 70 wt % of methacrylic acid, and optionally up to 40 wt % of a further comonomer,
  mixed polymers of 50 to 75 wt % ethyl acrylate, 25 to 35 wt % acrylic acid, and 0 to 25 wt % of other comonomers.

Suitable dispersions of this type are commercially available, for example under the tradename LATEKOLL® manufactured by BASF.

copolymers of 50 to 60 wt % ethyl acrylate, 30 to 40 wt % methacrylic acid, and 5 to 15 wt % acrylic acid, crosslinked with ethylene glycol dimethacrylate.

Particularly preferred copolymers are copolymers of acrylic acid, methacrylic acid or their $C_1$-$C_4$ alkyl esters, as are commercialized under the INCI name Acrylates Copolymers. In this regard, the combination of methacrylic acid and ethyl acrylate as well as optionally crosslinking, multifunctional monomers is preferred. A preferred commercial product for this is for example ACULYN® or 33A from the Rohm & Haas Company.

However, particularly good gel formation and stable viscosity control and ease of manufacture are obtained with the use of polyacrylic acid itself.

Another preferred example of the first subject matter of the present specification is therefore characterized in that the agent includes polyacrylic acid (such as a Carbomer) as the polymeric thickener.

The polymeric thickener(s) are preferably included in the agents according to the present specification in an amount of 0.1 to 5.0 wt %, preferably 0.3 to 3.0 wt %, particularly preferably 0.5 to 2.5 wt % and in particular 1.0 to 2.0 wt %, relative to the total weight of the agent.

A preferred agent according to the present specification has a gel-like carrier that includes 0.2 to 2.5 wt % non-ionic, polyethoxylated emulsifiers, 0.2 to 2.5 wt % polyethylene glycols, and 0.2 to 2.0 wt % polymeric thickener, each relative to the total weight of the agent.

Another preferred agent according to the present specification has a gel-like carrier that includes 0.2 to 2.5 wt % Ceteareth-20, 0.2 to 2.5 wt % PEG 1500, and 0.2 to 2.0 wt % Acrylates Copolymer, each relative to the total weight of the agent.

Another preferred agent according to the present specification has a gel-like carrier that includes 0.2 to 2.5 wt % Ceteareth-30, 0.2 to 2.5 wt % PEG 1500 and 0.2 to 2.0 wt % Acrylates Copolymer, each relative to the total weight of the agent.

Another preferred agent according to the present specification has a gel-like carrier that includes 0.2 to 2.5 wt % Ceteareth-50, 0.2 to 2.5 wt % PEG 1500, and 0.2 to 2.0 wt % Acrylates Copolymer, each relative to the total weight of the agent.

Another preferred agent according to the present specification has a gel-like carrier that includes 0.2 to 2.5 wt % PEG-40 hydrogenated Castor Oil, 0.2 to 2.5 wt % PEG 1500, and 0.2 to 2.0 wt % Acrylates Copolymer, each relative to the total weight of the agent.

Another preferred agent according to the present specification has a gel-like carrier that includes 0.2 to 2.5 wt % PEG-60 hydrogenated Castor Oil, 0.2 to 2.5 wt % PEG 1500, and 0.2 to 2.0 wt % Acrylates Copolymer, each relative to the total weight of the agent.

Another preferred agent according to the present specification has a gel-like carrier that includes 0.2 to 2.5 wt % Ceteareth-20, 0.2 to 2.5 wt % PEG 1500, and 0.2 to 2.0 wt % Carbomer, each relative to the total weight of the agent.

Another preferred agent according to the present specification has a gel-like carrier that includes 0.2 to 2.5 wt % Ceteareth-30, 0.2 to 2.5 wt % PEG 1500, and 0.2 to 2.0 wt % Carbomer, each relative to the total weight of the agent.

Another preferred agent according to the present specification has a gel-like carrier that includes 0.2 to 2.5 wt % Ceteareth-50, 0.2 to 2.5 wt % PEG 1500, and 0.2 to 2.0 wt % Carbomer, each relative to the total weight of the agent.

Another preferred agent according to the present specification has a gel-like carrier that includes 0.2 to 2.5 wt % PEG-40 hydrogenated Castor Oil, 0.2 to 2.5 wt % PEG 1500, and 0.2 to 2.0 wt % Carbomer, each relative to the total weight of the agent.

Another preferred agent according to the present specification has a gel-like carrier that includes 0.2 to 2.5 wt % PEG-60 hydrogenated Castor Oil, 0.2 to 2.5 wt % PEG 1500, and 0.2 to 2.0 wt % Carbomer, each relative to the total weight of the agent.

A preferred agent according to the present specification has a gel-like carrier that includes 1.5 to 2.5 wt % non-ionic, polyethoxylated emulsifiers (i), 1.5 to 2.5 wt % polyethylene glycols, and 1.0 to 2.0 wt % polymeric thickener, each relative to the total weight of the agent.

Another preferred agent according to the present specification has a gel-like carrier that includes 1.5 to 2.5 wt % Ceteareth-20, 0.2 to 2.5 wt % PEG 1500, and 1.0 to 2.0 wt % Acrylates Copolymer, each relative to the total weight of the agent.

Another preferred agent according to the present specification has a gel-like carrier that includes 1.5 to 2.5 wt % Ceteareth-30, 1.5 to 2.5 wt % PEG 1500, and 1.0 to 2.0 wt % Acrylates Copolymer, each relative to the total weight of the agent.

Another preferred agent according to the present specification has a gel-like carrier that includes 1.5 to 2.5 wt % Ceteareth-50, 1.5 to 2.5 wt % PEG 1500, and 1.0 to 2.0 wt % Acrylates Copolymer, each relative to the total weight of the agent.

Another preferred agent according to the present specification has a gel-like carrier that includes 1.5 to 2.5 wt % PEG-40 hydrogenated Castor Oil, 1.5 to 2.5 wt % PEG 1500, and 1.0 to 2.0 wt % Acrylates Copolymer, each relative to the total weight of the agent.

Another preferred agent according to the present specification has a gel-like carrier that includes 1.5 to 2.5 wt % PEG-60 hydrogenated Castor Oil, 1.5 to 2.5 wt % PEG 1500, and 1.0 to 2.0 wt % Acrylates Copolymer, each relative to the total weight of the agent.

Another preferred agent according to the present specification has a gel-like carrier that includes 1.5 to 2.5 wt % Ceteareth-20, 1.5 to 2.5 wt % PEG 1500, and 1.0 to 2.0 wt % Carbomer, each relative to the total weight of the agent.

Another preferred agent according to the present specification has a gel-like carrier that includes 1.5 to 2.5 wt % Ceteareth-30, 1.5 to 2.5 wt % PEG 1500, and 1.0 to 2.0 wt % Carbomer, each relative to the total weight of the agent.

Another preferred agent according to the present specification has a gel-like carrier that includes 1.5 to 2.5 wt % Ceteareth-50, 1.5 to 2.5 wt % PEG 1500, and 1.0 to 2.0 wt % Carbomer, each relative to the total weight of the agent.

Another preferred agent according to the present specification has a gel-like carrier that includes 1.5 to 2.5 wt % PEG-40 hydrogenated Castor Oil, 1.5 to 2.5 wt % PEG 1500, and 1.0 to 2.0 wt % Carbomer, each relative to the total weight of the agent.

Another preferred agent according to the present specification has a gel-like carrier that includes 1.5 to 2.5 wt % PEG-60 hydrogenated Castor Oil, 1.5 to 2.5 wt % PEG 1500, and 1.0 to 2.0 wt % Carbomer, each relative to the total weight of the agent.

Finally, the agents according to the present specification include at least one oxidation dye precursor. The dyes according to the present specification preferably include at least one oxidation dye precursor of the developer type and at least one oxidation dye precursor of the coupler type. The oxidation dye precursors are preferably used in an amount of 0.005 to 20 wt %, preferably 0.05 to 5 wt %, and particularly preferably from 0.1 to 5 wt %, each relative to the ready-to-use oxidation dye.

The developer and coupler components may be employed in free form. For substances with amino groups, it may, however, be preferred to employ them in salt form, especially in the form of the hydrochlorides and hydrobromides or sulfates. Here, developer components and coupler components may be used in approximately molar amounts relative to one another. Although the molar use has also proven to be expedient, a certain excess of individual oxidation dye precursors is not disadvantageous, such that developer components and coupler components may be included in a molar ratio of 1:0.5 to 1:2.

Preferred developer components are selected from p-phenylenediamine, p-toluylenediamine, 2-(2-hydroxyethyl)-p-phenylenediamine, 2-(1,2-dihydroxyethyl)-p-phenylenediamine, N,N-bis-(2-hydroxy-ethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropane-2-ol, bis-(2-hydroxy-5-aminophenyl)methane, 1,3-bis-(2,5-diaminophenoxy)propane-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)-pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, as well as the physiologically acceptable salts of these compounds.

The developer components are preferably used in an amount of 0.005 to 20 wt %, preferably 0.1 to 5 wt %, in each case based on the ready-to-use oxidation dye.

Coupler components alone, in the context of the oxidative dyeing, may not form any significant coloration; rather they may be used in the presence of developer components. Therefore it is preferred that when using at least one coupler component, at least one developer component is also used.

Preferred coupler components are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)-ethanol, 1,3-bis(2,4-diaminophenoxy)propane, 1-methoxy-2-amino-4-(2-hydroxyethylamino)-benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or their physiologically acceptable salts.

The coupler components are preferably used in an amount of 0.005 to 20.0 wt %, preferably 0.1 to 5.0 wt %, in each case relative to the ready-for-use coloring agent.

The agents may further include at least one substantive dye as an additional color modifying component for nuancing the coloration. These are dyes that are directly absorbed onto the hair and may not require any oxidative process to develop the color. Examples of substantive dyes include nitrophenylenediamines, nitroaminophenols, azo dyes, anthraquinones or indophenols. The substantive dyes are each preferably employed in quantities of 0.001 to 20.0 wt %, relative to the total end-use preparation. Another example of the present specification is therefore characterized in that the agent additionally includes at least one substantive dye.

Preferred anionic substantive dyestuffs are compounds known under the international designations or trade names Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol blue and Tetrabromophenol blue.

Preferred cationic substantive dyes are cationic triphenylmethane dyes, such as for example Basic Blue 7, Basic Blue 26, Basic Violet 2 and Basic Violet 14, aromatic systems that are substituted with a quaternary nitrogen group, such as for example Basic Yellow 57, Basic Red 76, Basic Blue 99, Basic Brown 16 and Basic Brown 17, HC Blue 16 as well as substantive dyes that include a heterocycle that possesses at least one quaternary nitrogen atom, in particular Basic Yellow 16, Basic Orange 87 and Basic Red 31. The cationic substantive dyes that are commercialized under the trade name ARIANOR® are likewise quite particularly preferred cationic substantive dyes.

Non-ionic nitro and quinone dyes and neutral azo dyes are particularly suitable as non-ionic substantive dyes. Preferred non-ionic substantive dyes are the compounds known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

It is not required that each of the oxidation dyestuff precursors or the substantive dyestuffs be pure compounds. In fact, the hair colorants of the present specification, due to the manufacturing processes for the individual dyes, may include minor quantities of even more components, in so far as they have no detrimental influence on the coloration result or that they must be excluded on other grounds, e.g. toxicological.

In the case of the oxidative dyeing, the color development can in principle occur with atmospheric oxygen. However, it is preferred to use a chemical oxidizing agent, particularly when a lightening effect on human hair is desired in addition to the dyeing. This lightening effect may be desired independently of the dyeing method. Oxidizing agents that come under consideration are persulfates, chlorites, hypochlorites and in particular hydrogen peroxide or its addition products onto urea, melamine as well as sodium borate. According to the present specification, however, the color changing agent as the oxidation dyeing agent can also be applied to the hair together with a catalyst that activates the oxidation of the dye precursors, e.g., by atmospheric oxygen. Such catalysts are e.g. certain enzymes, iodides, quinones or metal ions.

When additional oxidizing agents are used, the actual dye is advantageously produced immediately before the application by mixing an agent of the present disclosure, including, in a previously described gel-like carrier, at least one oxidation dye precursor, as well as a preparation that includes the additional oxidizing agent, in particular hydrogen peroxide.

Hydrogen peroxide is preferably employed as the oxidizing agent. The ready-to-use agent preferably includes the hydrogen peroxide in an amount of 0.5 to 12 wt %, preferably 0.8 to 6 wt %, each relative to the ready-to-use agent.

Such oxidizing agent preparations are preferably aqueous, free-flowing oxidizing agent preparations. In this regard, preferred preparations are characterized in that the free-flowing oxidizing agent preparation, based on its weight, include 40 to 90 wt %, preferably 50 to 85 wt %, particularly preferably 55 to 80 wt % more preferably 60 to 77.5 wt % and particularly 65 to 75 wt % water.

In addition, it has proven advantageous, particularly when the oxidizing agent preparations are composed of oxidation coloring agents, that they include at least one stabilizer or complexant. In the context of the present specification, preferred chelating complexants are for example polycarboxylic acids, nitrogen-containing mono or polycarboxylic acids, especially ethylenediaminetetraacetic acid (EDTA), ethylenediaminedisuccinic acid (EDDS) and nitrilotriacetic acid (NTA), geminal diphosphonic acids, in particular 1-hydroxyethane-1,1-diphosphonic acid (HEDP), amino phosphonic acids such as ethylenediaminetetra(methylenephosphonic acid) (EDTMP), diethylenetriaminepenta(methylenephosphonic acid) (DTPMP), phosphonopolycarboxyic acids such as 2-phosphonobutane-1,2,4-tricarboxylic acid as well as cyclodextrins, alkali metal stannates (sodium stannate), alkali metal pyrophosphates (tetrasodium pyrophosphate, disodium pyrophosphate), alkali metal phosphates (sodium phosphate), and phosphoric acid.

The agents according to the present specification may include additional auxiliaries and additives.

Suitable agents according to the present specification can further include, besides the polymeric thickeners selected from homopolymers of acrylic acid or methacrylic acid and/or copolymers of acrylic acid or methacrylic acid with $C_1$-$C_4$ alkyl esters of acrylic acid or methacrylic acid, in addition at least one further thickener. In this way the rheology of the agent according to the present specification can be converted into the free-flowing system desired by the consumer.

The additional polymeric thickener preferably concerns a hydrophilic thickener. Employable polymeric thickeners are:
  synthetic polymers, in particular homopolymers or copolymers of acrylic acid, its salts or its alkyl esters, which have been cationically or anionically modified in the alkyl chain; polyacrylamide polymers, in particular homopolymers or copolymers of acrylamide and/or methacrylamide, which have optionally been cationically or anionically modified; and copolymers of acrylic acid and acrylamide;
  polysaccharidic polymers, such as for example algin, alginates, glucanes such as dextran, pullulan, curdlan, cellulose, laminarin, amylose or lichenin, traganthe, karaya gum, ghatti gum, agar, carrageenan, chitin, chitosan, gum Arabic, gellan, caroba gum, galactomannanes such as guar or locust bean flour, tamarind kernel flour or their derivatives;
  inorganic thickeners, in particular suitable electrolytes, such as sodium chloride or potassium chloride, layered silicates (polymeric, crystalline sodium disilicates) and magnesium aluminum silicate or Bentonites, particularly Smectites, such as Montmorillonite or Hectorite, which can also be optionally suitably modified;
  as well as their mixtures.

The thickening, polysaccharidic polymers in particular afford mild and storage-stable formulations. Accordingly, preferred polymeric thickeners are thickening, polysaccharidic polymers. In this regard, particularly preferred polysaccharides are polymers based on cellulose. In this respect, chemically modified celluloses, such as for example acetyl, methyl or ethyl celluloses, hydroxyalkyl celluloses or carboxyalkyl celluloses may be employed. Particularly preferred cellulose derivatives possess saccharidic side chains, such as for example xanthan. One example of the present specification is characterized in that the agent includes a polysaccharidic polymer, preferably xanthan, as the polymeric thickener.

preferred agents are characterized in that the additional polymeric thickener is included in an amount of 0.005 to 1.0 wt %, particularly 0.01 to 0.5 wt %, and quite particularly 0.05 to 0.3 wt %, each relative to the total weight of the agent.

Moreover, the agents according to the present specification may include additional surface-active substances, such as anionic surfactants, zwitterionic surfactants and/or amphoteric surfactants.

Suitable anionic surface-active substances are characterized by a water-solubilizing anionic group, such as for example a carboxylate, sulfate, sulfonate or phosphate group and a lipophilic alkyl group containing about 8 to 30 carbon atoms. In addition, the molecule may include glycol or polyglycol ether groups, ester, ether and amide groups as well as hydroxy groups. Exemplary suitable anionic surfactants are, each in the form of the sodium, potassium and ammonium, as well as the mono, di and trialkanolammonium salts containing 2 to 4 carbon atoms in the alkanol group:
  linear and branched fatty acids (soaps),
  ether carboxylic acids,
  acyl sarcosides, acyl taurides and/or acyl isethionates of fatty acids,
  mono- and dialkyl esters of sulfosuccinic acid with 8 to 24 carbon atoms in the alkyl group and mono-alkyl polyoxyethyl esters of sulfosuccinic acid with 8 to 24 carbon atoms in the alkyl group and 1 to 6 oxyethylene groups,
  linear alkane sulfonates, linear α-olefin sulfonates, and sulfonates of unsaturated fatty acids,
  α-sulfofatty acid methyl esters of fatty acids,
  alkyl sulfates and alkyl ether sulfates,
  mixtures of surface-active hydroxysulfonates,
  sulfated hydroxyalkyl polyethylene glycol ethers and/or hydroxyalkylene propylene glycol ethers,
  esters of tartaric acid and citric acid with alcohols, which represent the addition products of about 2-15 molecules of ethylene oxide and/or propylene oxide on fatty alcohols containing 8 to 22 carbon atoms,
  optionally ethoxylated alkyl and/or alkenyl ether phosphates,
  alkylene glycol esters of sulfated fatty acids,
  monoglyceride sulfates and monoglyceride ether sulfates.

In particular, the dyes according to the present specification additionally include anionic surfactants, selected from fatty acids, alkyl sulfates, alkyl ether sulfates and ether carboxylic acids containing 10 to 18 carbon atoms in the alkyl group and up to 12 glycol ether groups in the molecule.

Zwitterionic surfactants are designated as those surface-active compounds that carry at least one quaternary ammonium group and at least one carboxylate, sulfonate or sulfate group in the molecule. Particularly suitable zwitterionic surfactants are the so-called betaines, such as the N-alkyl-N,N-dimethylammonium glycinates, for example cocoalkyl-dimethylammonium glycinate, N-acyl-aminopropyl-N,N-dimethylammonium glycinates, for example cocoacylaminopropyldimethylammonium glycinate, and 2-alkyl-3-carboxymethyl-3-hydroxyethyl-imidazolines each with 8 to 18 carbon atoms in the alkyl or acyl group as well as the cocoacylaminoethylhydroxyethylcarboxymethyl glycinate. A preferred zwitterionic surfactant is the fatty acid amide derivative, known under the INCI name Cocamidopropyl Betaine.

Particularly preferred amphoteric surfactants are commercialized under the INCI name Disodium Cocoamphodipropionate with the trade names MIRANOL® C2M SF conc. (Rhodia), AMPHOTERGE® K-2 (Lonza) and MONATERIC® CEM-38 (Unichema).

The agent according to the present specification preferably include the anionic, amphoteric and zwitterionic surfactants in a total amount of 0.05 wt % to 30 wt %, particularly preferably 0.1 wt % to 20 wt %, each relative to the total weight of the agent.

Furthermore, the agents according to the present specification may include additional non-ionic surface-active substances in addition to the above described non-ionic emulsifiers. Such compounds are for example $C_{12}$-$C_{30}$ fatty acid mono and diesters of addition products of 1 to 30 moles ethylene oxide on glycerin; polyglycerin esters and alkoxylated polyglycerin esters, such as for example poly(3)glycerin diisostearate and poly(2)glycerin polyhydroxystearate; alkoxylated, preferably propoxylated and in particular ethoxylated, mono and diglycerides, such as for example glycerin monolaurate+20 EO (moles ethylene oxide) and glycerin monostearate+20 EO; amine oxides; sorbitol fatty acid esters and addition products of ethylene oxide on sorbitol fatty acid esters such as for example polysorbates, sorbitol monolaurate and sorbitol monolaurate+20 EO; sugar fatty acid esters and addition products of ethylene oxide on sugar fatty acid esters; addition products of ethylene oxide on fatty acid alkanolamides and fatty amines; fatty acid N-alkylglucamides; alkylphenols and alkylphenol alkoxylates with 6 to 21, in particular 6 to 15 carbon atoms in the alkyl chain and 0 to 30 ethylene oxide and/or propylene oxide moieties, such as for example nonylphenol+4 EO, nonylphenol+9 EO, octylphenol+3 EO and octylphenol+8 EO, as well as alkyl polyglycosides. Alkyl mono and oligoglycosides and their ethoxylated analogs are particularly suitable as the non-ionic surfactants. Those alkyl polyglycosides of the Formula RO—(Z)$_x$, in which R consists essentially of $C_8$-$C_{18}$ alkyl groups, are preferred. Any mono or oligosaccharide, such as glucose, fructose, galactose, arabinose and sucrose, can be employed as the sugar building block Z. Glucose is particularly preferred. The alkyl polyglycosides used according to the specification include on average 1.1 to 5 sugar units. The additional non-ionic surfactants are preferably employed in quantities of 0.1 to 45 wt %, preferably 1 to 30 wt % and quite particularly preferably from 1 to 20 wt %, relative to the total amount of the ready-for-use agent.

Furthermore, the agents may include cationic surfactants of the type quaternary ammonium compounds, esterquats and amido amines, such as stearamidopropyldimethylamine. Preferred quaternary ammonium compounds are ammonium halides, such as alkyltrimethylammonium chlorides, dialkyldimethylammonium chlorides and trialkylmethylammonium chlorides, as well as the compounds known under the INCI names Quaternium-27 and Quaternium-83. The quaternized protein hydrolysates illustrate further inventively usable cationic surfactants. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines (trade names STEPANTEX®, DEHYQUART® and ARMOCARE®). The agents used according to the present specification preferably include the cationic surfactants in quantities of 0.05 to 10 wt %, based on the total agent. Quantities of 0.1 to 5 wt % are particularly preferred.

Moreover, the agents according to the present specification may include additional active substances, auxiliaries and additives, such as for example non-ionic polymers, cationic polymers, zwitterionic and amphoteric polymers, structurants such as glucose, maleic acid and lactic acid, hair conditioning compounds such as phospholipids, active substances for improving the fiber structure, in particular mono, di and oligosaccharides such as for example glucose, galactose, fructose, fruit sugar and lactose, defoamers such as silicones, preferably Dimethicon, light protective agents, proteins and protein hydrolysates, which have optionally been modified, active substances such as panthenol, pantothenic acid, pantolactone, allantoin, pyrrolidinone carboxylic acids and their salts such as bisabolol, vitamins, provitamins and vitamin precursors, in particular those of the groups A, $B_3$, $B_5$, $B_6$, C, E, F and H, plant extracts, swelling and penetration substances such as glycerin, propylene glycol monoethyl ether, carbonates, hydrogen carbonates, guanidines, ureas such as primary, secondary and tertiary phosphates and antioxidants.

These additional materials may be selected as a function of the desired properties of the agent. With regard to further optional ingredients and their amounts used, reference is expressly made to the relevant handbooks, for example the monograph by K. Schräder, Grundlagen and Rezepturen der Kosmetika, 2nd edition, Hüthig Buch Verlag, Heidelberg, 1989.

The agents according to the first subject matter of the present specification preferably exhibit a pH in the range 7 to 11 in order to stabilize the dye precursors and to ensure a stable gel formation. In the context of the present specification, the pH values refer to those measured at a temperature of 25 degrees Celsius (° C.).

Acidifiers and alkalizers are used to adjust the pH. The useable alkalizers for adjusting the pH of the agent to the preferred pH may be selected from the group formed from basic amino acids, amines, ammonia, alkali metal hydroxides, alkali metal metasilicates, alkali metal phosphates and alkali metal hydrogen phosphates. Preferred acidifiers are food acids, such as for example citric acid, acetic acid, malic acid or tartaric acid, as well as diluted mineral acids.

As already mentioned the agents according to the present specification may also be produced from two or more separately packaged preparations immediately prior to use. This lends itself in particular to the separation of incompatible ingredients in order to avoid premature reaction. A separation into multi-component systems is particularly appropriate in cases where incompatibilities of the ingredients are to be expected or feared. In systems of this type, the ready-to-use agent is produced by the user by blending the components immediately prior to use. A coloring agent, in which the oxidation dye precursors are initially separated from the oxidizing agent preparation that preferably includes hydrogen peroxide, is preferred in this regard.

Due to their specific carrier basis, the coloring agents according to the present specification possess significant advantages over other agents in regard to their rheological properties. In particular, the agents according to the present specification are characterized by a high storage-stability. The agents maintain a stable viscosity without any significant increase and in particular without a decrease in the viscosity, which could lead to considerable storage and application problems. This stability particularly applies to the preparation that includes the oxidation dye precursors, but also to the ready-to-use agent after blending the oxidizing agent preparation and the preparation that includes the oxidation dye precursors.

Moreover, the transparency of the carrier enables the progress of the dyeing procedure to be well monitored and brought to a stop by rinsing out the remaining agent when the desired coloration has been achieved. The colorations with the agents according to the present specification also lead to more intensive coloration results than with customary cream formulations of hair dyes. This also means that for the same coloration result, the amounts of dye in the agent according to the present specification may be significantly reduced compared with customary cream formulations.

A second subject matter of the present specification is a kit of parts, containing at least two containers assembled separately from one another. A first container includes at least one oxidation dye precursor in a gel-like carrier. The gel-like carrier of the agent includes:
at least one emulsifier combination including:
one or more non-ionic, polyethoxylated emulsifiers selected from ethoxylated fatty alcohols containing 8 to 22 carbon atoms, ethoxylated castor oil, or combinations thereof,
one or more polyethylene glycol(s) having an average molecular weight of 100 to 100,000 g mol$^{-1}$, and
at least one polymeric thickener selected from homopolymers of acrylic acid or methacrylic acid, copolymers of acrylic acid or methacrylic acid with $C_1$-$C_4$ alkyl esters of acrylic acid or methacrylic acid, or combinations thereof.

A second container contains an oxidizing agent preparation including at least hydrogen peroxide in a physiologically acceptable carrier.

If a particularly strong lightening effect is desired by adding peroxodisulfate salts, then it is preferred to add them to the kit of parts in the form of an optionally dedusted powder or in the form of a compression molded object as a separately packed, additional component. As used in the present specification and in the appended claims "a container" is understood to mean an encasement that exists in the form of an optionally reclosable bottle, a can, a small bag, a sachet or similar encasement. In this regard, the encasement can be made of plastic, glass, (metal) sheet, cardboard, paper or a composite material.

Furthermore, the kit of parts additionally includes instructions for use. Moreover, it can be preferred that an application aid, such as for example a comb or a brush or a blending bowl, and/or a personal protection kit, such as for example disposable gloves, is also supplied with the kit.

With reference to further preferred examples of the multi-component kit-of-parts, any statement made concerning the agents according to the present specification applies mutatis mutandis.

A further subject matter of the present specification is a method for dyeing human hair. The method includes:
blending an agent of the present specification with an oxidizing agent preparation immediately before application to form a ready-to-use agent. The oxidizing agent preparation including at least hydrogen peroxide in a physiologically acceptable carrier;
applying the ready-to-use agent onto the hair;
leaving the ready-to-use agent on the hair for a period of 5 to 45 minutes, preferably 15 to 35 minutes; and
rinsing the hair.

In the method, the agent of the present specification includes at least one oxidation dye precursor in a gel-like carrier. The gel-like carrier includes:
at least one emulsifier combination that includes:
one or more non-ionic, polyethoxylated emulsifiers selected from ethoxylated fatty alcohols containing 8 to 22 carbon atoms and/or ethoxylated castor oil, and
one or more polyethylene glycol(s) with an average molecular weight of 100 to 100,000 g mol$^{-1}$, and
and at least one polymeric thickener selected from homopolymers of acrylic acid or methacrylic acid and/or copolymers of acrylic acid or methacrylic acid with $C_1$-$C_4$ alkyl esters of acrylic acid or methacrylic acid.

A further subject matter of the present specification is also a method for dyeing human hair, in which an agent is produced immediately prior to the application by blending the components of the kit of parts described as the second subject matter of the present specification to form a ready-to-use agent. The ready-to-use agent is applied onto the hair, is left on the hair for a contact time of 2 to 45 minutes, preferably 15 to 35 minutes, and then the hair is rinsed out.

The application temperatures for the dyeing method according to the present specification may be in a range between 15 and 45° C. After the contact time, the hair dye is removed from the hair being dyed by rinsing, optionally with the help of a shampoo. There is no need to wash the hair with a shampoo if a strong surfactant-containing carrier, e.g. a color enhancing shampoo, was used.

With reference to further preferred examples of the method according to the present specification, any statement made concerning the agents according to the present specification applies mutatis mutandis.

Another subject matter of the present specification is the use of an optically transparent, gel-like carrier, including at least one oxidation dye precursor, for controlling the needs-based contact time of the agent when dyeing human hair.

The transparency of the carrier enables the progress of the dyeing procedure to be well monitored and brought to a stop by rinsing out the remaining agent, such that the contact time can be determined in a needs-based manner.

In a preferred example of this subject matter of the present specification, the gel-like carrier includes at least one polymeric thickener, such as for example polysaccharides or (meth)acrylic acid (co)polymers, in addition to oxidation dye precursor(s). In this regard, particularly preferred gel-like carriers include a polymeric thickener, selected from homopolymers of acrylic acid or methacrylic acid and/or copolymers of acrylic acid or methacrylic acid with $C_1$-$C_4$ alkyl esters of acrylic acid or methacrylic acid.

In another preferred example of this subject matter of the present specification, the gel-like carrier includes at least one non-ionic, polyethoxylated emulsifier, preferably selected from ethoxylated fatty alcohols containing 8 to 22 carbon atoms and/or ethoxylated castor oil, in addition to oxidation dye precursor(s).

In another preferred example of this subject matter of the present specification, the gel-like carrier further includes at least one polyethylene glycol with an average molecular weight of 100 to 100,000 g mol$^{-1}$, in addition to oxidation dye precursor(s).

For increasing the transparency of the carrier, combinations of at least one previously described non-ionic, polyethoxylated emulsifier and at least one polyethylene glycol with an average molecular weight of 100 to 100,000 g mol$^{-1}$ are particularly preferred.

In order to guarantee the stability and thereby finally the transparency of such gel-like carriers, particularly preferred gel-like carriers include:

at least one emulsifier combination that includes:
  one or more non-ionic, polyethoxylated emulsifiers selected from ethoxylated fatty alcohols containing 8 to 22 carbon atoms and/or ethoxylated castor oil, and
  one or more polyethylene glycol(s) with an average molecular weight of 100 to 100,000 g mol$^{-1}$, and
and at least one polymeric thickener selected from homopolymers of acrylic acid or methacrylic acid and/or copolymers of acrylic acid or methacrylic acid with $C_1$-$C_4$ alkyl esters of acrylic acid or methacrylic acid.

With reference to further preferred examples of the use according to the present specification, any statement made concerning the agents according to the present specification applies mutatis mutandis.

EXAMPLES

The examples that follow indicate agents that were produced for increasing the production of dyes. Unless otherwise indicated, all values in the tables that follow are in weight percent.

TABLE (1)

| Raw material | E1 | E2 | V1 | V2 |
|---|---|---|---|---|
| SYNTHALEN ® K | 0.90 | 1.20 | 1.20 | — |
| ACULYN ® 28 | — | — | — | 3.50 |
| Polyethylene glycol 1500 | 1.50 | 1.90 | — | 2.80 |
| PEG-40 hydrogenated castor oil | 1.30 | 1.80 | 1.80 | 1.30 |
| Glycerin | — | — | — | 11.20 |
| 1,2-Propane diol | — | — | — | 6.00 |
| Sodium sulfite, anhydrous, 96% | 0.20 | 0.20 | 0.20 | 0.20 |
| p-Toluenediamine sulfate | 0.11 | 0.11 | 0.11 | 0.11 |
| Resorcinol | 0.022 | 0.022 | 0.022 | 0.022 |
| 2-Methylresorcinol | 0.018 | 0.018 | 0.018 | 0.018 |
| 3-Aminophenol | 0.004 | 0.004 | 0.004 | 0.004 |
| 2-Amino-3-hydroxypyridine | 0.012 | 0.012 | 0.012 | 0.012 |
| Ascorbic acid | 0.05 | 0.05 | 0.05 | 0.05 |
| EDTA | 0.20 | 0.20 | 0.20 | 0.20 |
| Ammonia | 6.00 | 6.00 | 6.00 | 6.00 |
| Perfume | qs | qs | qs | qs |
| Water | ad 100 | ad 100 | ad 100 | ad 100 |

TABLE (2)

| Raw material | E3 | E4 | V3 | V4 |
|---|---|---|---|---|
| SYNTHALEN ® K | 0.90 | 1.20 | 1.20 | — |
| ACULYN ® 28 | — | — | — | 3.50 |
| Polyethylene glycol 1500 | 1.50 | 1.90 | — | 2.80 |
| PEG-40 hydrogenated castor oil | 1.30 | 1.80 | 1.80 | 1.30 |
| Glycerin | — | — | — | 11.20 |
| 1,2-Propane diol | — | — | — | 6.00 |
| Sodium sulfite, anhydrous, 96% | 0.20 | 0.20 | 0.20 | 0.20 |
| p-Toluenediamine sulfate | 0.062 | 0.062 | 0.062 | 0.062 |
| Resorcinol | 0.024 | 0.024 | 0.024 | 0.024 |
| 3-Aminophenol | 0.005 | 0.005 | 0.005 | 0.005 |
| 2-(2,4-Diaminophenoxy)ethanol 2HCl | 0.004 | 0.004 | 0.004 | 0.004 |
| Ascorbic acid | 0.05 | 0.05 | 0.05 | 0.05 |
| EDTA | 0.20 | 0.20 | 0.20 | 0.20 |
| Ammonia | 12.00 | 12.00 | 12.00 | 12.00 |
| Perfume | qs | qs | qs | qs |
| Water | ad 100 | ad 100 | ad 100 | ad 100 |

In Tables (1) and (2) SYNTHALEN® K is a polyacrylic acid (3V Sigma) that may be available under the INCI name Carbomer and ACULYN® 28 is a 20 wt % active substance (Rohm & Haas) that may be available under the INCI name Acrylates/Beheneth-25 Methacrylate Copolymer. In Tables (1) and (2) preparations E1, E2, E3, and E4 were agents according to the present specification and preparations V1, V2, V3, and V4 were control preparations.

The agents E2 and E4 were characterized by a viscosity that was suitable for the application requirements, whereas the agents E1 and E3 as well as V2 and V4, although still having an acceptable viscosity, were however overall slightly too fluid. Whereas the preparations E1, E2, E3 and E4 and the non-inventive agents V2 and V4 formed clear gels, the agents V1 and V3 were each cloudy and thus unsuitable for the monitoring of a dyeing reaction.

The dyes E1, E2, E3 and E4 as well as V1, V2, V3 and V4 were each blended prior to the application with a developer preparation EZ in the ratio 1:1.

TABLE (3)

| Raw material | EZ |
|---|---|
| NaOH, 45 wt % | 0.73 |
| Dipicolinic acid | 0.10 |
| Disodium pyrophosphate | 0.03 |
| Etidronic acid, 60 wt % | 1.50 |
| 1,2-Propane diol | 4.00 |
| Xanthan gum | 2.00 |
| Hydrogen peroxide, 50 wt % | 18.20 |
| Water | ad 100 |

It was determined that the application mixtures E1/EZ, E2/EZ, E3/EZ and E4/EZ on the one hand could be well mixed by stirring and afforded a clear, gel-like coloration preparation, wherein the application mixtures E2/EZ and E4/EZ had an optimum viscosity for the application. The combinations of V1/EZ, V2/EZ, V3/EZ and V4/EZ could not be satisfactorily stirred together to form suitable application mixtures.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for dyeing keratinic fibers, comprising, in a gel-like carrier at least one oxidation dye precursor, in which the gel-like carrier of the dye comprises:
   at least one emulsifier combination comprising:
      one or more non-ionic polyethoxylated emulsifiers selected from ethoxylated fatty alcohols containing between 8 and 22 carbon atoms, ethoxylated castor oil, or combinations thereof; and
      one or more polyethylene glycols having an average molecular weight between 100 and 100,000 grams per mole (g-MOL$^{-1}$); and
   at least one polymeric thickener selected from:
      homopolymers of acrylic acid or methacrylic acid;
      copolymers of acrylic acid or methacrylic acid with $C_1$-$C_4$ alkyl esters of acrylic acid or methacrylic acid; or
      combinations thereof.

2. The agent of claim 1, in which the gel-like carrier is optically transparent.

3. The agent of claim 1, in which the agent is free of fats.

4. The agent of claim 1, in which the non-ionic polyethoxylated emulsifiers comprise ethoxylated castor oil having a mean degree of ethoxylation between 20 and 150.

5. The agent of claim 1, in which the non-ionic polyethoxylated emulsifiers comprise ethoxylated castor oil having a mean degree of ethoxylation between 30 and 100.

6. The agent of claim 1, in which the non-ionic polyethoxylated emulsifiers comprise PEG-40 hydrogenated castor oil.

7. The agent of claim 1, in which the polyethylene glycol has an average molecular weight of between 500 and 15,000 g-MOL$^{-1}$.

8. The agent of claim 1, in which the polyethylene glycol has an average molecular weight of between 1,000 and 10,000 g-MOL$^{-1}$.

9. The agent of claim 1, in which the one or more polyethylene glycol includes at least one of PEG-30, PEG-32, PEG-35, PEG-38, PEG-40, PEG-45, PEG-50, PEG-60, PEG-75, PEG-80, PEG-100, PEG 1000, PEG 1200, PEG 1500, PEG 2000, PEG 3000, PEG 5000, and PEG 6000.

10. The agent of claim 1, in which a weight ratio of a fraction of the non-ionic polyethoxylated emulsifiers to a fraction of the polyethylene glycol in the emulsifier combination is between 3:1 and 1:3.

11. The agent of claim 1, in which a weight ratio of a fraction of the non-ionic, polyethoxylated emulsifiers to a fraction of the polyethylene glycol in the emulsifier combination is between 2:1 and 1:2.

12. The agent of claim 1, in which the emulsifier combination forms between 0.5 to 15.0 weight percent (wt %) of the agent.

13. The agent of claim 1, in which the emulsifier combination forms between 1.0 to 10.0 weight percent (wt %) of the agent.

14. The agent of claim 1, in which the emulsifier combination forms between 1.5 to 7.5 weight percent (wt %) of the agent.

15. The agent of claim 1, in which the polymeric thickener comprises a polyacrylic acid.

16. The agent of claim 1, in which the polymeric thickener forms between 0.1 to 5.0 weight percent (wt %) of the agent.

17. The agent of claim 1, in which the polymeric thickener forms between 0.3 to 3.0 weight percent (wt %) of the agent.

18. The agent of claim 1, in which the gel-like carrier comprises:
   between 0.2 and 2.5 weight percent (wt %) of the non-ionic polyethoxylated emulsifiers;
   between 0.2 and 2.5 wt % of the polyethylene glycols; and
   between 0.2 and 2.0 wt % of the polymeric thickener;
   each relative to a total weight of the agent.

19. A kit for dyeing keratinic fibers, the kit comprising at least two containers assembled separately from one another, in which:
   a first container holds an agent comprising, in a gel-like carrier at least one oxidation dye precursor, in which the gel-like carrier comprises:
      at least one emulsifier combination comprising:
         one or more non-ionic polyethoxylated emulsifiers, selected from ethoxylated fatty alcohols containing between 8 and 22 carbon atoms, ethoxylated castor oil, or combinations thereof; and
         one or more polyethylene glycols having an average molecular weight between 100 and 100,000 grams per mole (g-MOL$^{-1}$); and
      at least one polymeric thickener, selected from:
         homopolymers of acrylic acid or methacrylic acid;
         copolymers of acrylic acid or methacrylic acid with $C_1$-$C_4$ alkyl esters of acrylic acid or methacrylic acid; or
         combinations thereof; and
   a second container holds an oxidizing agent preparation comprising at least hydrogen peroxide in a physiologically acceptable carrier.

20. A method for dyeing human hair, the method comprising:
   blending an agent with an oxidizing agent preparation before application to form a ready-to-use agent, in which:
      the agent comprises, in a gel-like carrier, at least one oxidation dye precursor, in which the gel-like carrier comprises:
         at least one emulsifier combination comprising:
            one or more non-ionic polyethoxylated emulsifiers, selected from ethoxylated fatty alcohols containing between 8 and 22 carbon atoms, ethoxylated castor oil, or combinations thereof; and
            one or more polyethylene glycols having an average molecular weight between 100 and 100,000 grams per mole (g-MOL$^{-1}$); and
         at least one polymeric thickener, selected from:
            homopolymers of acrylic acid or methacrylic acid;
            copolymers of acrylic acid or methacrylic acid with $C_1$-$C_4$ alkyl esters of acrylic acid or methacrylic acid; or
            combinations thereof; and
      the oxidizing agent preparation comprises at least hydrogen peroxide in a physiologically acceptable carrier;
   applying the ready-to-use agent onto the hair;
   leaving the ready-to-use agent on the hair for a period of 5 to 45 minutes; and
   rinsing the hair.

* * * * *